(12) United States Patent
Pringgosusanto et al.

(10) Patent No.: US 12,023,639 B2
(45) Date of Patent: Jul. 2, 2024

(54) FLOWABLE CORE-SHELL MICROENCAPSULE COMPOSITION

(71) Applicant: INTERNATIONAL FLAVORS & FRAGRANCES INC., New York, NY (US)

(72) Inventors: Franklin Albert Pringgosusanto, Union Beach, NJ (US); Francis Michael Marks, III, Cambridge, MA (US); Christopher Lavallee, Union Beach, NJ (US); Lewis Michael Popplewell, Union Beach, NJ (US)

(73) Assignee: INTERNATIONAL FLAVORS & FRANGRANCES INC., New York, NY (US)

( * ) Notice: Subject to any disclaimer, the term of this patent is extended or adjusted under 35 U.S.C. 154(b) by 378 days.

(21) Appl. No.: 16/552,134

(22) Filed: Aug. 27, 2019

(65) Prior Publication Data

US 2021/0060511 A1    Mar. 4, 2021

(51) Int. Cl.
*B01J 13/04*    (2006.01)

(52) U.S. Cl.
CPC .................. *B01J 13/043* (2013.01)

(58) Field of Classification Search
CPC ........ A61K 8/11; A61K 2800/56; A61K 8/84; A61K 2800/412; A61K 2300/00; A61K 8/87; A61K 2800/10; A61K 8/731; A61K 8/8158; A61K 8/37; A61K 8/922; A61K 8/40; A61K 9/5089; A61K 8/361; A61K 8/416; A61K 8/8152; A61K 9/0014; A61K 9/5026; A61K 9/5031; A61K 2800/624; A61K 2800/654; A61K 31/327; A61K 47/14; A61K 8/31; A61K 8/35; A61K 8/41; A61K 8/65; A61K 8/737; A61K 8/88; A61K 8/891; A61K 9/501; A61K 2800/5426; A61K 31/133; A61K 31/155; A61K 31/198; A61K 31/216; A61K 31/277; A61K 31/4409; A61K 31/496; A61K 8/25; A61K 8/33; A61K 8/34; A61K 8/365; A61K 8/8111; A61K 8/817; A61K 8/8176; A61K 8/85; A61K 8/86; A61K 9/06; A61K 2800/22; A61K 2800/49; A61K 2800/524; A61K 2800/542; A61K 2800/5428; A61K 2800/592; A61K 2800/805; A61K 31/165; A61K 31/192; A61K 31/203; A61K 31/704; A61K 31/7052; A61K 31/7056; A61K 47/02; A61K 47/10; A61K 47/44; A61K 8/068; A61K 8/347; A61K 8/38; A61K 8/42; A61K 8/463; A61K 8/73; A61K 8/8117; A61K 8/91; A61K 9/00; A61K 9/08; A61K 9/107; A61K 9/1075; A61K 9/4816; A61K 9/4858; A61K 2800/244; A61K 2800/30; A61K 2800/413; A61K 2800/434; A61K 2800/438; A61K 2800/48; A61K 2800/52; A61K 2800/5424; A61K 2800/59; A61K 2800/591; A61K 2800/594; A61K 2800/652; A61K 2800/77; A61K 2800/80; A61K 2800/81; A61K 2800/95; A61K 45/06; A61K 47/08; A61K 47/34; A61K 47/42; A61K 8/00; A61K 8/022; A61K 8/0245; A61K 8/0275; A61K 8/042; A61K 8/19; A61K 8/26; A61K 8/342; A61K 8/36; A61K 8/375; A61K 8/39; A61K 8/43; A61K 8/442; A61K 8/46; A61K 8/466; A61K 8/49; A61K 8/4926; A61K 8/494; A61K 8/4946; A61K 8/4973; A61K 8/4986; A61K 8/604; A61K 8/64; A61K 8/645; A61K 8/732; A61K 8/736; A61K 8/738; A61K 8/8105; A61K 8/8135; A61K 8/8164; A61K 8/8182; A61K 8/8188; A61K 8/92; A61K 8/9789; A61K 9/5005; A61K 9/5015; A61K 9/5084; B01J 13/043
See application file for complete search history.

(56) References Cited

U.S. PATENT DOCUMENTS

| | | | | |
|---|---|---|---|---|
| 5,324,444 A | * | 6/1994 | Berry ................. | A61K 8/11 252/381 |
| 9,334,468 B2 | | 5/2016 | Sunder | |
| 2004/0022821 A1 | * | 2/2004 | Holzner ............. | A61K 8/494 424/401 |
| 2014/0066357 A1 | * | 3/2014 | Yao .................... | B01J 13/16 512/2 |

FOREIGN PATENT DOCUMENTS

EP    2419499 B1    3/2017

OTHER PUBLICATIONS

Powder Flow, 2016, Harmonization 30(6), from https://www.usp.org/sites/default/files/usp/document/harmonization/gen-chapter/g05_pf_30_6_2004.pdf (Year: 2016).*
National Filter Media, Candle filter basics and components, Mar. 2019, National filter media, from https://www.nfm-filter.com/blog/candle-filter-basics-and-components/ (Year: 2019).*

* cited by examiner

*Primary Examiner* — Bethany P Barham
*Assistant Examiner* — Ayaan A Alam

(57) ABSTRACT

A method for producing a flowable active material-encapsulated core-shell microcapsule composition by mechanically removing solvent from a microcapsule suspension to produce a wet cake, and subsequently charging the wet cake with a dry flow aid, is provided.

10 Claims, No Drawings

FLOWABLE CORE-SHELL MICROENCAPSULE COMPOSITION

BACKGROUND

Fragranced powder is used in many different applications, such as powder detergent, and dry stick deodorant among others. There are several methods to achieve this, including spray drying. Typically, spray dry formulations are composed of modified starches, gum Arabic, maltodextrins, and/or various sugars. In some cases, microcapsules can also be included, which provide an additional shear release benefit to the powder. See US 2014/0044761 A1 and US 2014/0287008 A1. A disadvantage of adding microcapsules to dry products is that the microcapsules are suspended in an aqueous solution, which, when blended with a consumer product, can result in agglomeration and clumping and partial dissolving of water-soluble components of the consumer product. While EP 2419499 B1 and U.S. Pat. No. 9,334,468 B2 describe the addition of specific water absorbing materials to bind the water in the microcapsule slurry, the total water content of the microcapsule slurry is not decreased. Needed is a means for decreasing the water content of a microcapsule slurry so that a dry product is produced, which is stable and has good flowability. The present invention addresses this need in the art.

SUMMARY OF THE INVENTION

This invention provides a method for producing a flowable core-shell microcapsule composition by removing, from a suspension composed of a solvent and active material-encapsulated core-shell microcapsules, a substantial portion of the solvent by mechanical separation (e.g., centrifugation, filtration, evaporation, or a combination thereof) to produce a wet cake; and charging the wet cake with a dry flow aid using, e.g., a conical mixer, ribbon blender, tumbler mixer, granulator, or high shear mixer. Active materials of use in the core-shell microcapsule composition include, e.g., a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellent, vermin repellent, emollient, skin moisturizing agent, wrinkle control agent, UV protection agent, fabric softener active, hard surface cleaning active, skin or hair conditioning agent, flame retardant, antistatic agent, taste modulator, cell, probiotic, colorant, vegetable oil, and combinations thereof. Furthermore, the shell of the core-shell microcapsules can be composed of a urea-formaldehyde polymer, a melamine-formaldehyde polymer, a phenolic-formaldehyde polymer, a urea-glutaraldehyde polymer, a melamine-glutaraldehyde polymer, a phenolic-glutaraldehyde polymer, polyurea, polyurethane, polyacrylate, polyamide, polyester, an epoxy cross-linked polymer, a polyfunctional carbodiimide cross-linked polymer, silica, a silica-derived material, or a combination thereof as wall material. Dry flow aids suitable for use in this invention include metal salts of a hydroxide, oxide, oxide hydrate, borate, carbonate, sulfate, phosphate, phosphite, hypophosphite, silicate, stearate, or a combination thereof.

The flowable core-shell microcapsule composition can be characterized by one or more of the following features: the active material is from 5% to 90% (e.g., preferably 10% to 80%, and more preferably 45% to 60%) by weight of the flowable core-shell microcapsule composition; the core-shell microcapsules are from 20% to 90% (e.g., preferably 30% to 80%, and more preferably 50% to 75%) by weight of the flowable core-shell microcapsule composition; the dry flow aid is from 5% to 40% (preferably 8% to 30%, and more preferably 10% to 20%) by weight of the flowable core-shell microcapsule composition; the water content of the flowable core-shell microcapsule composition is in the range of 0% to 40% by weight (e.g., 0 to 30%); the flowable core-shell microcapsule composition has a Hausner ratio in the range of to 1.25; and/or the flowable core-shell microcapsule composition has a minimum ignition energy of greater than 10 mJ. The core-shell microcapsule composition is flowable when its Hausner ratio is 1.25 or less.

Also, within the scope of this invention are consumer products including the flowable core-shell microcapsule composition.

DETAILED DESCRIPTION OF THE INVENTION

Conventionally, spray dry technologies are used in the preparation of dry products such as powder detergent and deodorant. In many instances, microcapsules are needed for protecting benefit agents from degradation and/or loss and/or the requirement for a shear release benefit, which cannot be achieved without the use of microcapsules. However, spray drying to produce a dry microcapsule product has a number of cost and safety challenges. In particular, spray dried products are fine and dry and can contain up to 60% oil. This combination presents an explosion hazard (due to static) in manufacturing plants where the powder is blended into the products that customers use. To reduce the explosion risk, a salt can be incorporated into the spray dry process. However, in addition to diluting the oil load, the inclusion of a salt increases the cost associated with the spray dry technology.

The present method addresses the need in the art for dry microcapsule compositions by mechanically removing liquid from a microcapsule suspension. In particular, this invention is a method for producing a dry microcapsule composition by separating or removing, from a suspension composed of active material-encapsulated core-shell microcapsules and a solvent, a substantial portion of the solvent via mechanical separation to produce a wet cake and charging the wet cake with a dry flow aid. Advantageously, the method of this invention does not require or include the use of absorbent materials such as salts, clays, or zeolites and/or spray drying to bind or remove large amounts of water from a microcapsule suspension. Once produced, the dry microcapsule composition of this invention can be dry-blended with one or more other powders or anhydrous products without adding a significant amount of water to the product. In this manner, the dry microcapsule composition of this invention allows for a simpler and more economical process than adding a liquid microcapsule slurry to a dry powder product.

As used herein, the phrase "active material" refers to an ingredient having a desired activity, e.g., therapeutic, cosmetic, cosmeceutical, cleaning, or sensory benefit. It is contemplated that any active material, which can be encapsulated in a core-shell microcapsule, can be used in the composition and method of this invention. An active material may include, but is not limited to, a fragrance, pro-fragrance, flavor, malodor counteractive agent, vitamin or derivative thereof, anti-inflammatory agent, fungicide, anesthetic, analgesic, antimicrobial active, anti-viral agent, anti-infectious agent, anti-acne agent, skin lightening agent, insect repellant, animal repellant, vermin repellant, emollient, skin moisturizing agent, wrinkle control agent, UV protection agent, fabric softener active, hard surface cleaning active, skin or hair conditioning agent, flame retardant, antistatic agent, taste modulator, cell, probiotic, colorant, vegetable oil, and combinations thereof. In certain embodiments, the active material is a fragrance, pro-fragrance, malodor counteractive agent, wrinkle control agent, or fabric softener active. In particular embodiments, the active material is one or a combination of fragrances.

In accordance with this invention, the active material is encapsulated in core-shell microcapsules, referred to herein as "active material-encapsulated core-shell microcapsules." As the term implies, a "core-shell microcapsule" refers to a generally spherical shell of water-insoluble and/or oil-insoluble materials, typically a network polymer material, within which an active material is contained. Encapsulation of active materials is known in the art, see for example U.S. Pat. Nos. 2,800,457, 3,870,542, 3,516,941, 3,415,758, 3,041,288, 5,112,688, 6,329,057, and 6,261,483. Wall forming materials include urea-formaldehyde polymer, a melamine-formaldehyde polymer, a phenolic-formaldehyde polymer, a urea-glutaraldehyde polymer, a melamine-glutaraldehyde polymer, a phenolic-glutaraldehyde polymer, polyurea, polyurethane, polyacrylate, polyamide, polyester, an epoxy cross-linked polymer, a polyfunctional carbodiimide cross-linked polymer, silica, a silica-derived material, or a combination thereof as wall material. Additionally, microcapsules can be made via the simple or complex coacervation of gelatin. Preferred encapsulating polymers include those formed from urea-formaldehyde, melamine-formaldehyde, isocyanates, silica, or hydrogel-forming polymers.

Polyurea and polyurethane core-shell microcapsules may be prepared by interfacial polycondensation. See e.g., U.S. Pat. Nos. 6,797,670 and 10,092,486. Such wall materials are produced by having an oil phase which includes a polyfunctional isocyanate, e.g., a polyisocyanate having two or more isocyanate groups, and a second aqueous phase which includes (i) a polyfunctional alcohol (i.e., a polyol) having two or more —OH groups for obtaining a polyurethane capsule wall, or (ii) a polyfunctional amine (i.e., a polyamine) having two or more —$NH_2$ and/or —NH groups for obtaining a polyurea capsule wall.

Urea-formaldehyde and melamine-formaldehyde microcapsules may be prepared by reacting urea or melamine with formaldehyde optionally in the presence of a cross-linking agent. Methods for formation of such melamine-formaldehyde and urea-formaldehyde pre-condensates are described in U.S. Pat. Nos. 3,516,846, 6,261,483, and Lee, et al. (2002) *J. Microencapsulation* 19:559-569.

Silica or sol-gel microcapsules may be prepared by subjecting a sol-gel precursor to a polymerization reaction (e.g., hydrolyzation). Suitable sol-gel precursors are compounds capable of forming gels such as compounds containing silicon, boron, aluminum, titanium, zinc, zirconium, and vanadium.

Active material-encapsulated core-shell microcapsules prepared by any one of the above-described methods are produced in the form of a slurry or suspension, referred to generally herein as a "microcapsule suspension" or "microcapsule slurry," wherein the microcapsules are suspended in a solvent, e.g., water. In accordance with the present method, a substantial portion of the solvent is removed using one or more mechanical separation techniques. Alternatively stated, the microcapsule suspension is dewatered. A "substantial portion" of solvent is defined as an amount by weight of solvent that is reduced by at least 55%, 60%, 70%, 80%, or 90%, or in a range between any combination of these amounts. Alternatively stated, the removal of a substantial portion of solvent means that the resulting wet cake is composed of less than 40%, 35%, 30%, 25%, 20%, 15%, or 10% by weight of solvent (in which the microcapsules are suspended), or a range between any combination of these amounts.

"Mechanical separation" refers to a group of laboratory and/or production operations whereby the components of a polyphase mixture are separated by mechanical methods into two or more fractions of different characteristics. The separated fractions may be homogeneous or heterogeneous, particulate or nonparticulate. In accordance with the present invention, a substantial portion of solvent is removed from a microcapsule suspension. As such, the resulting fractions include (a) the solvent and (b) the active material-encapsulated core-shell microcapsules in a substantially reduced amount of solvent (i.e., the wet cake).

Mechanical separation techniques for removing solvent from a microcapsule suspension include centrifugation, filtration, evaporation, or a combination thereof (e.g., centrifugal filters). Mechanical separation can be achieved by continuous or discontinuous (e.g., batch) operations. In some aspects, mechanical separation is achieved by centrifugation using a basket, peeler, and/or inverted centrifuge. In certain aspects, the solvent is removed or separated from the microcapsule suspension by filtration (i.e., use of a filter). Useful filtration equipment includes a rotary vacuum, pressure leaf, press, nutsche or candle filter. In certain embodiments, mechanical separation of solvent from the microcapsule suspension is carried out by candle filtration, grain separation, vacuum filtration, pressure filtration, nutsche filtration, rotary drum filtration or a combination thereof. In particular embodiments, candle filtration is used to produce a wet cake.

The mechanical separation technique may be selected based upon compatibility with the mechanical properties of the particular core-shell microcapsules of the microcapsule suspension so that the core-shell microcapsules are not ruptured, punctured, lost, or otherwise stressed to prematurely release active material from the core. By way of illustration, whereas a polyurea microcapsule may withstand the pressure of a candle filter, rotary drum filtration may be more suitable for microcapsule with a gelatin wall.

To improve one or more characteristics of the active material-encapsulated core-shell microcapsule composition, the wet cake is charged with a dry flow aid. In the context of a "dry flow aid," the term "dry" means that the flow aid has a moisture content of less than 10%, 5%, 4%, 3%, 2% or 1% by weight of the flow aid and/or water activity of less than about 0.5, 0.4, 0.3, or 0.2 prior to being added to the wet cake.

A "flow aid" refers to any substance that reduces particle-to-particle attraction or sticking, such as through electrostatic or mechanical means thereby providing a stable, agglomerate-free powder with consistently useful flowability. The dry flow aid is added in an amount effective to minimize or eliminate clumping and the presence of flakes in the microcapsule composition. Ideally, the flow aid of the invention has a median particle size of from 5 nm to 200 µm. The preferred median particle size of the flow aid is from 10 nm to 150 µm, particularly preferably from 100 nm to 100 µm. In addition, it is desirable that the flow aid has a specific surface area of from 20 $m^2/g$ to 600 $m^2/g$. The flow aid preferably has a specific surface area of from 40 $m^2/g$ to 550 $m^2/g$, particularly preferably from 60 $m^2/g$ to 500 $m^2/g$, and more preferably from 60 $m^2/g$ to 450 $m^2/g$.

In some aspects, the dry flow aid is a metal salt of a hydroxide, oxide, oxide hydrate, borate, carbonate, sulfate, phosphate, phosphite, hypophosphite, silicate, stearate, or a combination thereof. Exemplary flow aids include, but are not limited to, magnesium oxide or hydroxide, aluminum oxide, aluminum oxide hydroxide, tin oxide, antimony oxide (III and V) and oxide hydrate, titanium oxide, and zinc oxide or oxide hydrate, zirconium oxide and/or zirconium hydroxide, zinc borate, calcium carbonate, magnesium carbonate, barium sulfate, sodium sulfate, calcium sulfate, boron phosphate, zinc phosphate, monoammonium phosphate, aluminum hydrogen phosphite, melem or a melamine metal phosphate, magnesium silicates, sodium silicate, potassium silicate, calcium silicate, aluminosilicate, silica, sodium stearate and the like.

In certain aspects, the flow aid includes one or more silicate or silica flow aids. The one or more silica flow aids may be precipitated silica, a pyrogenic (fumed) silica, hydrophilic silica, amorphous silica, synthetic silica, hydrophobic silica or a combination thereof. In certain embodiments, the silicate is a submicron-sized silicon dioxide. A preferred fumed silica is available under the tradename AEROSIL® 200, a hydrophilic silica with a tapped density of 50 g/L. A preferred synthetic amorphous silica is available under the tradename SYLOID® 244.

The wet cake may be charged (e.g., blended or mixed) with a dry flow aid using one or a combination of dry mixing techniques. Mixing can be continuous or batch and the mixing equipment may be selected from the group of a conical mixer, ribbon blender, tumbler mixer, granulator, or high shear mixer. As with the mechanical separation technique, the dry mixing technique may be selected based upon compatibility with the mechanical properties of the particular core-shell microcapsules of the wet cake so that the core-shell microcapsules are not ruptured, punctured, lost, or otherwise stressed to prematurely release active material from the core.

The dry or dewatered active material-encapsulated core-shell microcapsule composition, also referred to herein as a "flowable core-shell microcapsule composition" or simply "flowable microcapsule composition," which is produced by the method of this invention has a number of characteristics that distinguish the dry microcapsule composition from those described in the literature. In particular, given the substantial reduction in water content, the relative amount of microcapsules, and load or relative amount of active material is increased compared to a conventional microcapsule slurry. In particular, the active material of the flowable core-shell microcapsule composition of this invention is in the range of from 5% to 90% by weight (e.g., 20% to 80%, by weight, or most preferably from 45% to 60% by weight of the flowable core-shell microcapsule composition.

Similarly, the microcapsules of the flowable core-shell microcapsule composition of this disclosure are present in an amount ranging from 20% to 90% by weight, preferably 30% to 80% by weight, or most preferably from 50% to 75% by weight of the flowable core-shell microcapsule composition.

The dry flow aid of the flowable core-shell microcapsule composition of this disclosure is present in an amount ranging from 5% to 40% by weight, preferably 8% to 30% by weight, or more preferably from 10% to about 20% by weight of the flowable core-shell microcapsule composition.

The dewatered or dry active ingredient-encapsulated core-shell microcapsule composition of this invention has a water content of less than 60%, preferably less than 40%, or more preferably less than 35%, 30%, 25%, or 20% by weight of the flowable core-shell microcapsule composition. Alternatively stated, the dry active ingredient-encapsulated core-shell microcapsule composition of this invention has a water content in the range of 0% to 60% (e.g., 40% or less, 36% or less, 5% to 40%, and 10% to 35%) by weight of the flowable core-shell microcapsule composition.

If not otherwise specified, the amounts of the components of the flowable core-shell microcapsule composition are based upon the total weight of the flowable core-shell microcapsule composition.

The flowable core-shell microcapsule composition has a particle size in diameter ranging from 1 micron to 200 microns, preferably from 1 micron to 100 microns, and more preferably from 1 micron 40 microns.

Contrary to flowable powders, which use absorbent materials such as salts, clays, or zeolites and/or spray drying to bind or remove large amounts of water from a microcapsule suspension, the present invention provides an agglomerate-free powder with consistently useful flowability by mechanically removing water from a microcapsule suspension. Four techniques are commonly used to assess powder flowability: angle of repose; compressibility (Carr's) index and Hausner ratio; flow through an orifice; and shear cell methods. For the latter two no general scales have been developed due to diversity of methodology. Flow through an orifice can be used to measure flow rate or alternatively to determine a critical diameter that allows flow. Pertinent variables are the shape and diameter of the orifice, the diameter and height of the powder bed, and the material the apparatus is made of. Shear cell devices include cylindrical, annular, and planar varieties and offer great degree of experimental control. For either of these two methods, description of the equipment and methodology are crucial, but despite the lack of general scales they are successfully used to provide qualitative and relative characterizations of powder flowability.

Angle of repose is determined as the angle assumed by a cone-like pile of the material relative to a horizontal base upon which it has been poured. Hausner ratio is the unsettled volume divided by the tapped volume (that is the volume after tapping produces no further change in volume), or alternatively the tapped density divided by the bulk density. The compressibility index (CI) can be calculated from the Hausner ratio (HR) as: $CI=100\times(1-(1/HR))$.

Despite some variation in experimental methods generally accepted scales of flow properties have been published for angle of repose, compressibility index and Hausner ratio (Table 1; Carr (1965) *Chem. Eng.* 72:163-168).

TABLE 1

| Flow Character | Angle of Repose | Hausner Ratio | Compressibility Index (%) |
|---|---|---|---|
| Excellent | 25-30° | 1-1.11 | ≤10 |
| Good | 31-35° | 1.12-1.18 | 11-15 |
| Fair | 36-40° | 1.19-1.25 | 16-20 |
| Passable | 41-45° | 1.26-1.34 | 21-25 |
| Poor | 46-55° | 1.35-1.45 | 26-31 |
| Very Poor | 46-65° | 1.46-1.59 | 32-37 |
| Very, Very Poor | ≥65° | ≥1.6 | ≥38 |

Powders with a flow character according to the table above that are excellent or good can be characterized in terms of cohesiveness as non- or minimally cohesive, and the powders with less flowability as cohesive and further dividing them between moderately cohesive (corresponding to fair or passable flow character) and highly cohesive (corresponding to any degree of poor flow character). Dry active material-encapsulated core-shell microcapsule compositions in each of these ranges, or combinations thereof, constitute aspects of distinct embodiments of the invention. In certain embodiments, the dry active material-encapsulated core-shell microcapsule has a Hausner ratio below 1.6, 1.46, 1.35, 1.26, 1.19 or 1.12. More preferably, the dry active material-encapsulated core-shell microcapsule composition has a Hausner ratio in the range of 1 to 1.6, or more desirably in the range of 1 to 1.35, or most desirably in the range of 1 to 1.25.

A number of the flow aids of this disclosure also provide flame retardant or fireproofing activity. For example, U.S. Pat. No. 7,204,998 teaches that sodium silicate, potassium silicate and monoammonium phosphate exhibit fireproofing activity. Accordingly, in certain aspects, the dry active material-encapsulated core-shell microcapsule composition has a minimum ignition energy of >10 mJ. MIE testing on powders or dusts can be performed to determine the smallest electric spark that can ignite a dust-cloud atmosphere at its most easily ignitable concentration (in air). The sensitivity of the dust cloud to ignition is influenced by particle size and moisture content. A reduction in particle size and/or moisture content result in a dust cloud that is more sensitive to ignition.

Advantageously the method of this invention provides a final dry product with a yield of microcapsules in the range of about 50% to about 100%, preferably about 60% to about 99%, or more preferably from about 70% to about 95% of the initial microcapsule suspension. Therefore, this is a highly efficient method for producing a flowable core-shell microcapsule composition of use in a number of consumer products. Accordingly, in addition to a flowable core-shell microcapsule composition produced by the method of this disclosure, the present invention also provides a consumer product including said flowable core-shell microcapsule composition.

Consumer products to which the instant dry microcapsule composition can be incorporated include, but are not limited to, fabric care products such as conditioners, powder detergents and scent boosters; home care products such as all-purpose cleaners and fabric refreshers; personal hygiene products such as hand sanitizers, deodorants and antiperspirants, dry shampoos, hair refreshers, and body powder products; and oral care products such as tooth powder, all of which are known in the art. When included in a consumer product, the dry active material-encapsulated core-shell microcapsule composition may be added as a single ingredient to the consumer product. Alternatively, prior to addition to the consumer product, the dry active material-encapsulated core-shell microcapsule composition may be combined with one or more additional ingredients. Such additional ingredients include, e.g., builders, surfactants, polymers, bleaching agents, bleach activators, bleach catalysts, enzymes, disintegration aids, fragrances, perfume carriers, colorants, electrolytes, pH adjustors, fluorescence agents, hydrotropes, foam inhibitors, silicone oils, anti-redeposition agents, optical brighteners, anti-graying inhibitors, shrink preventers, anti-creasing agents, color-transfer inhibitors, antimicrobials, germicides, fungicides, antioxidants, antistats, ironing auxiliaries, water-proofing and impregnation agents, swelling and non-slip agents as well as UV-absorbers.

The following non-limiting examples are provided to further illustrate the present invention.

Example 1: Candle Filtration for Producing a Flowable Core-Shell Microcapsule Composition Slurries of core-shell microcapsules were prepared using a large-scale batch reaction system capable of high shearing to form an emulsion between an aqueous phase containing the wall material and an oil phase containing the fragrance oil. Additional reactants such as cross-linking agents were added and the fragrance-encapsulated core-shell microcapsules were cured.

After the microcapsules were cured, the resulting microcapsule slurries were separated by candle filtration to produce a wet cake. More specifically, the microcapsule slurries were fed into a FUNDABAC® candle filter fitted with a polypropylene filter cloth having an average pore size of 1.5 micron. While water and particles smaller than 1.5 microns passed through the filter as waste, the fragrance-encapsulated core-shell microcapsules were collecting around the candle filter and dried by passing through the chamber compressed air or nitrogen that drives residual water out. Once this was complete, the dried capsules were discharged as wet cake.

The wet cake was composed of moisture and core-shell microcapsules. On average, the water content of the wet cake was below 40% and fragrance load was 50% or more by weight of the wet cake. Cake thickness was dependent on the slurry formulation and component ratios, filter size, filtration time, filtration pressure, and capsule size, but did not exceed the capacity of the filter chamber.

After discharge from the candle filter, the wet cake was charged with a dry flow aid. Specifically, up to 20 wt % of a combination of two forms of silicon dioxide, SYLOID® 244 (micron-sized synthetic silica) and AEROSIL® 200 (finely divided silica), were mixed with the wet cake using a ribbon blender until full incorporation and reduction of large solids occurred. As ensure flowability, intermittent sampling was carried out during blending until a Hausner ratio of less than 1.25 was achieved. The addition of dry flow aid lowered the remaining water content of the final product, and increased stability and flow dynamics. The final dry powder had a water content below 40% and a fragrance load near 50%. Optionally, neat oil was added to the dry flow aid, prior to addition of the wet cake, to increase the overall fragrance load of the final product up to 60%. An overview of the process is presented in FIG. 1.

Example 2: Analytical Assessments

Using the method described in Example 1, six microcapsule slurries (MS-1 to MS-4) were prepared with three different fragrances FR1, FR2, and FR3. See Table 2. Using a series of analytical and sensory testing, characteristics of the wet cakes and flowable core-shell microcapsule compositions were determined. Briefly, after removing a portion of the aqueous phase by candle filtration with variable filtration times, a wet cake (P1-P4) was produced and parameters such as water content (tested using the Karl Fisher titration, see e.g., WO 2010/131207 A1), capsule loss and free oil amounts were measured (Table 2).

TABLE 2

| Sample | Fragrance | Fragrance in slurry (%) | Filtration Time (min.) | Water (%) | Capsule Loss (%) |
|---|---|---|---|---|---|
| P1 | FR1 | 32 | 240 | 21.97 | 4.46 |
| P2 | FR2 | 32 | 8.67 | 28.46 | 5.11 |
| P3 | FR3 | 40 | 4 | 35.53 | 1.05 |
| P4 | FR3 | 38.75 | 5 | 35.53 | 1.7 |

The results of this analysis indicated that the aqueous phase was reduced to less than 36% (e.g., between 17% and 36%). In addition, capsule loss was approximately 5% or less, while free oil was negligible (<0.1%) indicating that there was no rupturing of the capsules throughout the filtration process.

Wet cakes P1-P4 each were then blended with silicon dioxide using a ribbon blender or conical screw mixer to obtain flowable core-shell microcapsule compositions S1-S4 of this invention. See Table 3 below. Water content and flowability were assessed (Table 3).

TABLE 3

| Sample | SiO$_2$ (%) | Water (%) | Hausner Ratio |
|---|---|---|---|
| S1: P1 + SiO$_2$ | 11.8 | 16.09 | 1.22 |
| S2: P2 + SiO$_2$ | 13.8 | 19.97 | 1.23 |
| S3: P3 + SiO$_2$ | 14.3 | 28.55 | 1.22 |
| S4: P4 + SiO$_2$ | 14.3 | 23.72 | 1.23 |

SiO$_2$, mixture of SYLOID® 244 (micron-sized synthetic silica) and AEROSIL® 200 (finely divided silica).

The results of this analysis indicated that the addition of silicon dioxide further reduced the water content and improved flow dynamics with all Hausner ratios being below 1.25. P1-P4 were sticky, wet cake and not flowable. After mixing with silicon dioxide, they turned into flowable compositions.

The resulting dry fragrance-encapsulated core-shell microcapsule compositions S1-S4 were further subjected to sensory testing. In particular, flowable core-shell microcapsule compositions S1-S4, microcapsule slurries MS-3 and MS-4 (see Tables 1 and 2) were evaluated in a powder detergent and EU washing machine. Sensory evaluations were conducted at damp, pre-rub and post-rub. The results indicate high performance of flowable core-shell microcapsule compositions S1-S4.

Flowable core-shell microcapsule composition S1 was further tested for stability over seven days at high temperature and relative humidity (40° C./85% RH). S1 showed no clumping, discoloration or disintegration, and was still free flowing after the completion of the test under elevated conditions.

What is claimed is:

1. A method for producing a flowable core-shell microcapsule composition comprising:
   (a) removing, from a suspension composed of a solvent and core-shell microcapsules each encapsulating an active material, a substantial portion of the solvent by candle filtration to produce a wet cake; and
   (b) charging the wet cake with a compound selected from the group consisting of sodium silicate, potassium silicate, and monoammonium phosphate as a dry flow aid and flame retardant thereby producing a flowable core-shell microcapsule composition, wherein the flowable core-shell microcapsule composition has a minimum ignition energy of greater than 10 mJ.

2. A flowable core-shell microcapsule composition produced by the method of claim 1.

3. A consumer product comprising the flowable core-shell microcapsule composition of claim 2.

4. The method of claim 1, wherein the water content of the flowable core-shell microcapsule composition is in the range of 0% to 60% by weight.

5. The method of claim 1, wherein the flowable core-shell microcapsule composition has a Hausner ratio in the range of 1 to 1.25.

6. A method for producing a flowable core-shell microcapsule composition comprising:
   (a) removing, from a suspension composed of a solvent and core-shell microcapsules each encapsulating an active material, a substantial portion of the solvent by mechanical separation to produce a wet cake; and
   (b) charging the wet cake with a compound selected from the group consisting of sodium silicate, potassium silicate, and monoammonium phosphate as a dry flow aid and flame retardant thereby producing a flowable core-shell microcapsule composition, wherein the flowable core-shell microcapsule composition has a minimum ignition energy of greater than 10 mJ.

7. The method of claim 6, wherein the water content of the flowable core-shell microcapsule composition is in the range of 0% to 60% by weight.

8. The method of claim 6, wherein the flowable core-shell microcapsule composition has a Hausner ratio in the range of 1 to 1.25.

9. A flowable core-shell microcapsule composition produced by the method of claim 6.

10. A consumer product comprising the flowable core-shell microcapsule composition of claim 9.

* * * * *